United States Patent [19]
Judd

[11] Patent Number: 5,847,278
[45] Date of Patent: Dec. 8, 1998

[54] ACCELEROMETER WITH SHEAR ISOLATED MOUNTING

[75] Inventor: John E. Judd, Hamden, Conn.

[73] Assignee: Vibrametrics, Inc., Handen, Conn.

[21] Appl. No.: 818,328

[22] Filed: Mar. 14, 1997

[51] Int. Cl.[6] ................................................. G01P 15/08
[52] U.S. Cl. ........................... 73/493; 73/514.34; 73/654
[58] Field of Search ..................... 310/329, 333; 73/514, 34, 493, 497, 651, 652, 654, 1.38

[56] References Cited

U.S. PATENT DOCUMENTS

| | | |
|---|---|---|
| 4,211,951 | 7/1980 | Jensen . |
| 4,858,470 | 8/1989 | Kincaid et al. . |
| 4,884,250 | 11/1989 | Kirtzinger et al. . |
| 4,905,518 | 3/1990 | Kübler . |
| 5,130,600 | 7/1992 | Tomita et al. . |
| 5,212,984 | 5/1993 | Norling ..................................... 73/493 |
| 5,218,870 | 6/1993 | Komurasaki et al. . |
| 5,473,941 | 12/1995 | Judd et al. . |
| 5,677,487 | 10/1997 | Hansen ................................ 73/514.34 |

Primary Examiner—Christine K. Oda
Attorney, Agent, or Firm—DeLio & Peterson, LLC

[57] ABSTRACT

An accelerometer providing shear isolation from unwanted shear forces by means of a shear isolation member located inside the accelerometer housing. The shear isolation member is rigidly attached to the housing at a mounting end and one or more piezoelectric crystals are mounted on a crystal mounting region. The mounting end is sufficiently far from the crystal mounting region that shear forces exerted on the accelerometer housing are not transmitted through the mounting end to the crystal mounting region, while vibrations, which affect the entire accelerometer, produce shear forces in the crystal which are easily detected.

12 Claims, 1 Drawing Sheet

ACCELEROMETER WITH SHEAR ISOLATED MOUNTING

BACKGROUND OF THE INVENTION

1. Field of the Invention

This invention relates to accelerometers used to measure vibration. More particularly, the invention relates to center mounted accelerometers which have been specially designed to minimize the transmission of unwanted shear forces to the piezoelectric crystal sensor.

2. Description of Related Art

Accelerometers are widely used to monitor the vibration of electrical motors, pumps and the like in industrial applications, especially in continuous production operations. Changes in vibration levels, particularly in rotating machinery, provide an advance warning of problems such as excessive wear or an approaching bearing failure. With such warning, the problems can be dealt with during regularly scheduled maintenance periods and expensive unplanned shutdowns can be avoided.

In industrial applications of this type, accelerometers are exposed to numerous hazards. Accelerometers near pumps are often splashed by acids, coolants, caustic solvents, oils, hydraulic fluids or other industrial chemicals that over time migrate into a conventional accelerometer and cause it to fail.

Accelerometers monitoring electrical motors, or which are near industrial electrical equipment, are exposed to high levels of EMI/RFI noise that can seriously interfere with operation of the electrical components in the accelerometer. Interference may be radiated directly into the accelerometer or conducted in through the case and mounting bolts.

Ground loops are also a particular problem where grounded case accelerometers have been used. Attempts to alleviate such problems by isolation stud mounting (which electrically insulates the case of the accelerometer from the equipment being monitored) are often defeated in harsh environments as the exterior of the accelerometer and the isolation stud are contaminated over time by conductive industrial materials.

Further, manufacturing facilities are a notoriously rough location for sensitive monitoring equipment. Accelerometers mounted on industrial machinery may be exposed to high G-force impacts and other physical abuse. The cables connected to the accelerometers may be inadvertently pulled excessively, or bent to very sharp angles, leading to premature failure.

In view of these hazards, a popular type of accelerometer is the center mounted, Faraday shielded, fully encapsulated accelerometer of the type shown in U.S. Pat. No. 5,473,941. Accelerometers of this type are quite sensitive and yet are well protected against chemical and mechanical damage and against various types of electrical interference. Further, they have the convenient center mounting system in which the entire accelerometer may be rotated around its center mounting bolt so that the cable leading out of the accelerometer to the monitoring equipment may be positioned out of the way in a desired position.

The sensitivity of such accelerometers is achieved through the use of one or more piezoelectric crystal sensors mounted for shear mode sensing. Typically the piezoelectric crystal is mounted between an accelerometer mass on one side and the accelerometer housing on the other. The accelerometer housing is secured to the machinery to be monitored and vibrations are transmitted through the accelerometer housing to the crystal. The vibrations cause shear forces to be exerted on the piezoelectric crystal as a result of relative motion between the mass and the accelerometer housing. The shear forces distort the piezoelectric crystal, producing an electrical signal that is sensed by monitoring and recording equipment.

However, in addition to the vibration-induced shear forces that one wants to detect, there can be other sources of shear force on the piezoelectric crystal which produce undesired output signals. These undesired signals can mask or interfere with the vibration signal of interest. By way of example, cable motion can distort the accelerometer housing producing a shear force that is transmitted through the accelerometer housing to the piezoelectric crystal. Alternatively, the mounting bolt may produce an undesired shear force.

To avoid such problems and the deficiencies of the prior art, it is therefore an object of the present invention to provide an accelerometer with an improved mounting system for the piezoelectric crystal which provides shear isolation from undesired shear forces, while still responding to the vibration-produced shear forces of interest.

Yet another object of the present invention is to provide an accelerometer with good shear isolation from undesired shear forces which also is hermetically sealed, has excellent resistance to most industrial chemicals, is ground isolated, has excellent EMI/RFI resistance and includes an integral cable with superior cable bend and strain relief protection.

Still other objects and advantages of the invention will in part be obvious and will in part be apparent from the specification.

SUMMARY OF THE INVENTION

The above and other objects, which will be apparent to those skilled in the art, are achieved in the present invention which is directed to an accelerometer which has a shear isolation member located inside an accelerometer housing. The housing has at least one mounting bolt opening for attaching the accelerometer to the object to be monitored and is preferably a toroidally shaped center mounted housing.

The shear isolation member is rigidly attached to the housing only at an end (the mounting end), and the remainder of the shear isolation member (the crystal mounting region) provides a location to mount one or more piezoelectric crystals. A mass is mounted on the opposite side of the crystal from the shear isolation member to operate the piezoelectric crystal in the shear mode. The mounting end is sufficiently far from the crystal mounting region that shear forces exerted on the accelerometer housing by the mounting bolt are not transmitted through the mounting end to the crystal mounting region, while vibrations, which affect the entire accelerometer produce shear forces in the crystal which are easily detected.

In the most highly preferred embodiment, the housing is electrically conductive, extending completely around the accelerometer to form a Faraday shield, and is encased within an electrically non-conductive encapsulant which hermetically seals the accelerometer against contaminants of all types and which electrically isolates the accelerometer from the mounting surface or equipment to which it is attached.

BRIEF DESCRIPTION OF THE DRAWINGS

The features of the invention believed to be novel and the elements characteristic of the invention are set forth with particularity in the appended claims. The figures are for illustration purposes only and are not drawn to scale. the invention itself, however, both as to organization and method of operation, may best be understood by reference to the detailed description which follows taken in conjunction with the accompanying drawings in which:

DESCRIPTION OF THE PREFERRED EMBODIMENT(S)

In describing the preferred embodiment of the present invention, reference will be made herein to FIGS. 1–2 of the drawings in which like numerals refer to like features of the invention.

Figure 1:
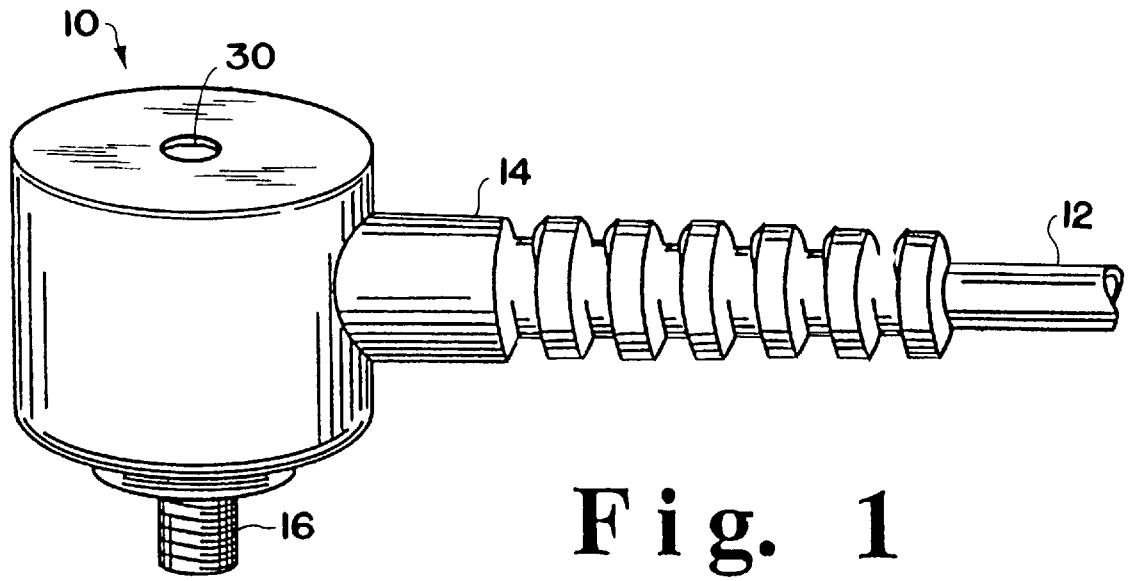
FIG. 1 is a perspective view of an accelerometer according to the present invention.

Referring to FIG. 1, the accelerometer generally includes an accelerometer contained within a housing 10. The housing is approximately doughnut-shaped, i.e. toroidally shaped, with a mounting bolt 16 passing through a mounting bolt opening 30. A connection cable 12 makes connection at one end to the accelerometer through a cable boot 14 which provides cable bend protection. A connector of any desired type (not shown) is connected to the other end of the cable 12.

Figure 2:
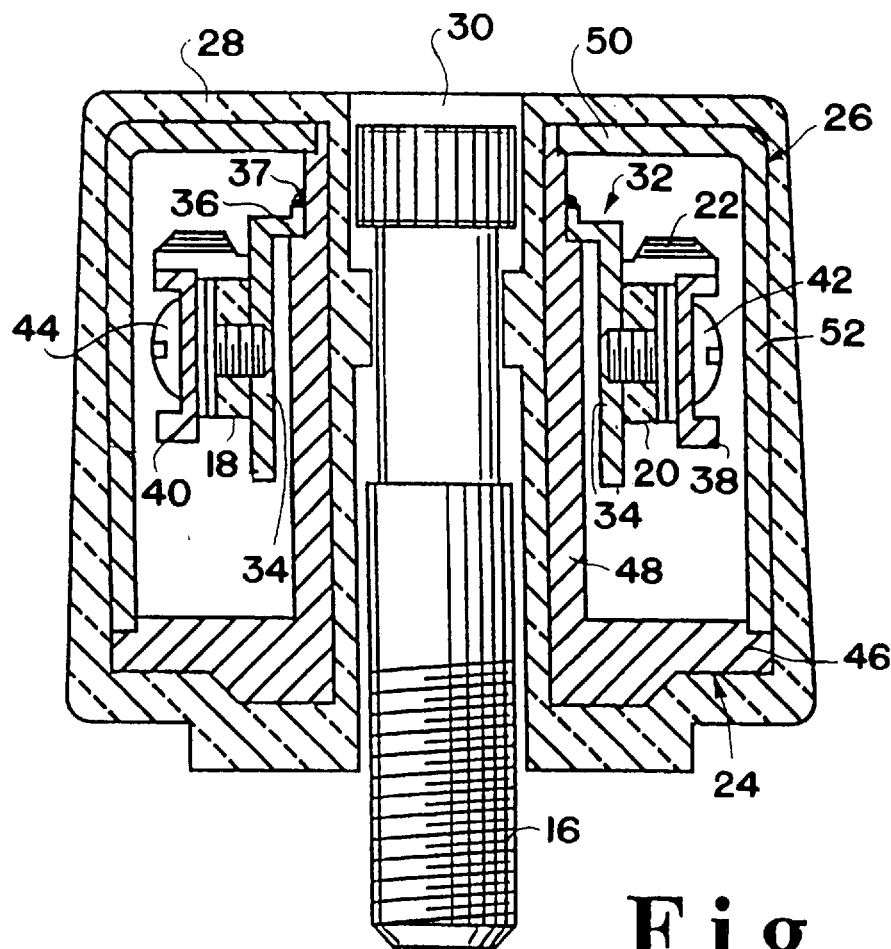
FIG. 2 is a cross sectional view of the accelerometer of the present invention taken in a plane perpendicular to the axis of the cable and through the axis of the mounting bolt.

Referring to the cross sectional view of FIG. 2, it can be seen that the principal working components of the accelerometer include a piezoelectric sensor composed of two piezoelectric crystal elements 18, 20 mounted on either side of the center opening and an electrical circuit 22 mounted on a ring shaped circuit board that surrounds the center opening.

In the preferred design, the circuit 22 includes impedance transforming means and an amplifier so that the circuit output has a low impedance. In the most highly preferred design, the circuit is provided with reverse voltage protection, temperature equalization and electrostatic discharge protection with known techniques.

The circuit 22 and piezoelectric crystal elements 18, 20 are mounted within a Faraday shield composed of a base 24 and a cap 26. The base 24 is composed of an annular base plate portion 46 and an inner cylindrical portion 48. The bottom of the inner cylindrical portion 48 is preferably integrally connected to the base plate portion 46. The cap 26 is composed of an annular top plate portion 50 and an outer cylindrical portion 52, which are also preferably integrally formed as a single piece. The inner and outer cylindrical portions 48, 52 are coaxially located when the two shield elements 24, 26 are assembled. The annular portions 46, 50 enclose the space between the cylindrical portions forming a squared-off torus (with vertical walls and a horizontal top and bottom) that completely surrounds and encases the circuit and piezoelectric elements.

The only opening in the shield is a small insulated pass through opening (not shown) through which the vibration signal is passed to the cable 12. The result of completely surrounding the circuit with a conductor is to form a Faraday shield that excludes EMI/RFI interference from the interior which might prevent proper operation.

The Faraday shield formed by the cap 24 and base 26 is in turn completely encapsulated within an electrically non-conductive encapsulating material 28. The encapsulating material electrically isolates the shield from the environment, including the mounting surface and the mounting bolt 16, to provide ground isolation and protect against the formation of ground loops.

The encapsulating material extends into the central opening of the shield to electrically isolate the mounting bolt 16 from the Faraday shield. The encapsulating material also traps the mounting bolt so that it will not become separated during shipping or handling, while still permitting it to rotate as necessary when the bolt is being fastened to the mounting surface.

Cable 12 is preferably a coaxial cable and the outer conductor (shield conductor) of the coaxial cable is connected to the Faraday shield. The center conductor of the coaxial cable 12 is connected to the circuit through the insulated pass through opening referred to above.

The boot 14 is pre-manufactured and slipped over the cable 12 and adhesively attached to provide cable bend protection at the joint between the cable 12 and the accelerometer 10.

As can be seen in FIG. 2, the encapsulating material 28 not only extends around the visible exterior of the device but also extends below the base portion 46 of the Faraday shield. This electrically isolates the accelerometer from the mounting surface to prevent ground loops and conducted EMI/RFI interference. The combination of the internal Faraday shield and case ground isolation provides excellent noise rejection for both radiated and conducted EMI/RFI noise.

In addition to providing strain relief and electrical isolation, the encapsulating material provides hermetic sealing and impact resistance. The hermetic sealing occurs as a result of the encapsulating process which applies the encapsulating material in a hot injection molding process, preferably at a pressure of 1,000 pounds per square inch (6.8× $10^6$ Pascals) or more.

The encapsulating material should have high impact strength, low flammability, high corrosion resistance, high flexural and tensile strength, high compressive strength, low moisture absorption, low heat distortion, high hardness, a broad operating temperature range from −65° F. to +400° F. (−54° to 204° C.) in addition to high electrical resistivity and excellent resistance to a broad range of chemical compounds including acids, alkaline coolants and caustic solvents, gear, brake and engine oils, hydraulic fluids and fuels as well as bleaches and chlorine. Appropriate materials include thermosetting plastics, vinylesters including glass fiber reinforced vinylesters, glass fiber reinforced polyesters and mineral filled epoxies. The preferred material, selected after considerable evaluation of alternatives, is a vinylester based product such as vinylester c108 manufactured by Industrial Dielectrics, Inc. of Noblesville, Ind.

The cable also requires certain properties to perform well in the harsh environments to which the accelerometers of the invention are exposed. These properties include good resistance to all the industrial chemicals referred to above, good high temperature characteristics in the temperature range to be expected during the injection molding process, high pull strength, good flexibility and excellent electrical shielding. High quality coaxial electrical cables employing insulation of fluorocarbon elastomers, tetrafluorethylene-propylene polymers and silicon are all suitable, with tetrafluorethylene-propylene polymers being slightly preferred.

The piezoelectric crystal elements 18, 20 are mounted on opposite sides of an approximately cylindrically shaped shear isolation member 32. The shear isolation member is composed of two crystal mounting subregions 34 and a mounting end 36 and is attached to the housing by weld 37. The piezoelectric crystal elements 18, 20 are mounted in the shear mode by being sandwiched between their respective crystal mounting subregion 34 and their respective mass 38 or 40. Screws 42, 44 pass through the masses and into the respective crystal mounting subregion 34 of the shear isolation member 32.

The accelerometer is described and shown herein in the preferred embodiment with two piezoelectric crystal elements, and wherein the shear isolation member includes first and second opposed crystal mounting subregions having the piezoelectric crystal elements mounted thereon. However, the shear isolation member of the present invention may also be used in a design having only a single piezoelectric crystal mounted in a single crystal mounting region.

Vibrations are transmitted through the housing 10 to the mounting end 36 of the shear isolation member 32 and down into the crystal mounting subregions 34. As the crystal mounting subregions move due to the vibrations, and as the masses 38, 40 resist being driven by the vibrations, shear forces develop in the piezoelectric crystals 18, 20 which produce the signals of interest.

The design of the shear isolation member 32 acts to provide shear isolation from unwanted shear forces to provide significantly improved operation as compared to previous accelerometer designs. In previous designs, the piezoelectric crystal elements were directly attached to the housing. As a result, shear forces produced in the housing produced unwanted shear in the crystals. Referring to FIG. 2, it can be seen that when the mounting bolt 16 is tightened, shear forces are developed in the inner cylindrical portion 48. Where the piezoelectric crystal elements are directly attached to the inner cylindrical portion, undesired signals are detected.

As another example, where the cable 12 is pulled sharply to one side as a result of not being properly fastened down or poor positioning during installation, it can place a twisting force on the housing. This twisting force also produces unwanted shear. During the active vibration of a machine being monitored, these and other sources of unwanted shear force on the housing may produce signals that mask the signal of interest in prior art accelerometer designs.

In the present design, all of these undesired shear forces in the housing are excluded by the shear isolation member 32. Because only one end of the shear isolation member, the mounting end 36, is rigidly attached to the housing, and because of the separation of the mounting end from the crystal mounting subregions, shear forces in the housing are poorly transmitted to the crystal mounting subregions. As a result, the shear forces in the piezoelectric crystals 18, 20 are almost exclusively due to the relative motion of the shear isolation member on one side of the crystal and the mass on the other side.

Those of skill in the art will recognize that it is the design of the shear isolation member 32 in which the rigid connection to the housing is placed at one end, at some distance from the crystal mounting region, which provides the desired shear isolation. Although the invention has been shown in the preferred configuration where the shear isolation member is cylindrically shaped, variations on this design are contemplated within the present invention, provided that they include a shear isolation member that transmits the vibrations, but substantially reduces the transmission of shear forces from the housing.

The Faraday shield and shear isolation member are preferably made of stainless steel, but may also be made of other electrically conductive materials. Welding the two together, as shown, provides an excellent rigid connection, but other connection methods are also suitable.

It will thus be seen that the objects set forth above, among those made apparent from the preceding description, are efficiently attained and, since certain changes may be made in the above construction(s) without departing from the spirit and scope of the invention, it is intended that all matter contained in the above description or shown in the accompanying drawing(s) shall be interpreted as illustrative and not in a limiting sense.

Thus, having described the invention, what is claimed is:

1. An accelerometer comprising:
   a housing having a mounting bolt opening adapted to receive a mounting bolt to attach the accelerometer to an object to be monitored;
   a shear isolation member located inside the housing having a crystal mounting region and a mounting end, the shear isolation member being rigidly attached to the housing by the mounting end to transmit vibrations to the crystal mounting region through the mounting end, the mounting end being sufficiently far from the crystal mounting region that shear forces exerted on the housing by the mounting bolt are not transmitted through the mounting end to the crystal mounting region, the crystal mounting region extending substantially parallel to the mounting bolt opening;
   a mass; and
   a piezoelectric crystal attached between the crystal mounting region of the shear isolation member and the mass to detect vibrations.

2. An accelerometer according to claim 1 wherein the mounting bolt opening extends through the housing and the shear isolation member surrounds the mounting bolt opening.

3. An accelerometer according to claim 2 wherein the mounting bolt opening is located in the center of the housing and wherein the shear isolation member is approximately cylindrical.

4. An accelerometer according to claim 2 wherein the housing is toroidally shaped, the mounting bolt opening extends centrally through the housing, and the shear isolation member is approximately cylindrical with the mounting bolt opening extending centrally through the cylindrical shear isolation member.

5. An accelerometer comprising:
   a toroidally shaped housing having a mounting bolt opening adapted to receive a mounting bolt to attach the accelerometer to an object to be monitored, the mounting bolt opening extending centrally through the housing;
   an approximately cylindrical shear isolation member located inside the housing and surrounding the mounting bolt opening, the shear isolation member having a crystal mounting region and a mounting end, the shear isolation member being rigidly attached to the housing by the mounting end to transmit vibrations to the crystal mounting region through the mounting end, the mounting end being sufficiently far from the crystal mounting region that shear forces exerted on the housing by the mounting bolt are not transmitted through the mounting end to the crystal mounting region;
   a mass; and
   a piezoelectric crystal attached between the crystal mounting region of the shear isolation member and the mass to detect vibrations;

the shear isolation member including an inwardly extending lip comprising the mounting end of the shear isolation member, the inwardly extending lip being rigidly attached to the toroidally shaped housing.

6. An accelerometer comprising:
   a toroidally shaped housing having a mounting bolt opening adapted to receive a mounting bolt to attach the accelerometer to an object to be monitored, the mounting bolt opening extending centrally through the housing;
   an approximately cylindrical shear isolation member located inside the housing and surrounding the mounting bolt opening, the shear isolation member having a crystal mounting region and a mounting end, the mounting end of the shear isolation member being welded to the housing to transmit vibrations to the crystal mounting region through the mounting end, the mounting end being sufficiently far from the crystal mounting region that shear forces exerted on the housing by the mounting bolt are not transmitted through the mounting end to the crystal mounting region;
   a mass; and
   a piezoelectric crystal attached between the crystal mounting region of the shear isolation member and the mass to detect vibrations.

7. An accelerometer according to claim 1 wherein the housing is electrically conductive and an encapsulant surrounds the housing, the housing extending substantially completely around the shear isolation member and completely around the piezoelectric crystal to prevent electromagnetic and radio frequency interference, and the encapsulant is electrically nonconductive, the encapsulant extending substantially completely around the housing.

8. An accelerometer comprising:
   an electrically conductive housing having a mounting bolt opening adapted to receive a mounting bolt to attach the accelerometer to an object to be monitored, the housing being surrounded by an electrically nonconductive encapsulant;
   a shear isolation member located inside the housing, the housing extending substantially completely around the shear isolation member, the shear isolation member having a crystal mounting region and a mounting end, the shear isolation member being rigidly attached to the housing by the mounting end to transmit vibrations to the crystal mounting region through the mounting end, the mounting end being sufficiently far from the crystal mounting region that shear forces exerted on the housing by the mounting bolt are not transmitted through the mounting end to the crystal mounting region;
   a mass;
   a piezoelectric crystal attached between the crystal mounting region of the shear isolation member and the mass to detect vibrations, the housing extending completely around the piezoelectric crystal to prevent electromagnetic and radio frequency interference;
   a cable extending into the accelerometer; and
   a cable sleeve including mechanical connection means engaged by and encapsulated within the encapsulant to provide strain relief for the cable.

9. An accelerometer according to claim 8 wherein the mounting bolt opening has an axis and the cable extends at right angles to the axis of the mounting bolt opening.

10. An accelerometer comprising:
    a housing having a mounting bolt opening adapted to receive a mounting bolt to attach the accelerometer to an object to be monitored;
    a shear isolation member located inside the housing having a crystal mounting region and a mounting end, the shear isolation member being rigidly attached to the housing by the mounting end to transmit vibrations to the crystal mounting region through the mounting end, the mounting end being sufficiently far from the crystal mounting region that shear forces exerted on the housing by the mounting bolt are not transmitted through the mounting end to the crystal mounting region, the crystal mounting region of the shear isolation member comprising first and second opposed crystal mounting subregions;
    a mass; and
    a piezoelectric crystal attached between the crystal mounting region of the shear isolation member and the mass to detect vibrations, the piezoelectric crystal being composed of first and second piezoelectric crystal elements mounted on the respective first and second crystal mounting subregions.

11. An accelerometer comprising:
    a housing having a mounting bolt opening adapted to receive a mounting bolt to attach the accelerometer to an object to be monitored, the housing including:
       a first element having an annular base plate portion and an inner cylindrical portion with a top and a bottom, the bottom of the inner cylindrical portion being connected to the base plate portion of the first element, and
       a second element having an annular top plate portion and an outer cylindrical portion with a top and a bottom, the top of the outer cylindrical portion being connected to the top plate portion;
       the first and second elements engaging one another to form the housing;
    a shear isolation member located inside the housing having a crystal mounting region and a mounting end, the shear isolation member being rigidly attached to the housing by the mounting end to transmit vibrations to the crystal mounting region through the mounting end, the mounting end being sufficiently far from the crystal mounting region that shear forces exerted on the housing by the mounting bolt are not transmitted through the mounting end to the crystal mounting region;
    a mass; and
    a piezoelectric crystal attached between the crystal mounting region of the shear isolation member and the mass to detect vibrations.

12. An accelerometer according to claim 1 wherein the mounting end of the shear isolation member is welded to the housing.

* * * * *

UNITED STATES PATENT AND TRADEMARK OFFICE
CERTIFICATE OF CORRECTION

PATENT NO. : 5,847,278

DATED : 12/8/98

INVENTOR(S) : Judd

It is certified that error appears in the above-identified patent and that said Letters Patent is hereby corrected as shown below:

Column 3, line 2, "the" should be --The--.

Signed and Sealed this

Twenty-third Day of March, 1999

Attest:

Q. TODD DICKINSON

*Attesting Officer*    *Acting Commissioner of Patents and Trademarks*